(12) United States Patent
Simpson

(10) Patent No.: US 11,298,170 B2
(45) Date of Patent: Apr. 12, 2022

(54) SPINAL IMPLANT SYSTEM AND METHODS OF USE

(71) Applicant: Warsaw Orthopedic, Inc., Warsaw, IN (US)

(72) Inventor: Joshua W. Simpson, Collierville, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 73 days.

(21) Appl. No.: 16/415,728

(22) Filed: May 17, 2019

(65) Prior Publication Data

US 2020/0360067 A1 Nov. 19, 2020

(51) Int. Cl.
*A61B 17/70* (2006.01)
*A61B 17/86* (2006.01)

(52) U.S. Cl.
CPC ...... *A61B 17/8685* (2013.01); *A61B 17/7032* (2013.01)

(58) Field of Classification Search
CPC .............. A61B 17/707; A61B 17/7002; A61B 17/7036; A61B 17/7074; A61B 17/7049; A61B 17/7052; A61B 17/7043; A61B 17/7098; A61B 17/8805; A61B 17/7035; A61B 17/7085; A61B 17/7086; A61B 17/7091; A61B 17/863; A61B 17/862; A61B 17/8605; A61B 17/7037; A61B 17/8883; A61B 17/8685; A61B 2017/00867; A61B 2017/0088; A61B 2017/00933; A61B 2017/00004; A61B 2017/564
See application file for complete search history.

(56) References Cited

U.S. PATENT DOCUMENTS

| | | | | |
|---|---|---|---|---|
| 5,667,508 | A * | 9/1997 | Errico | A61B 17/7032 606/301 |
| 6,540,749 | B2 * | 4/2003 | Schafer | A61B 17/701 606/265 |
| 6,626,908 | B2 * | 9/2003 | Cooper | A61B 17/7032 606/266 |
| 7,211,086 | B2 * | 5/2007 | Biedermann | A61B 17/7032 606/308 |
| 7,947,065 | B2 * | 5/2011 | Hammill, Sr | A61B 17/7038 606/267 |
| 9,456,851 | B2 * | 10/2016 | Richelsoph | A61B 17/7035 |
| 10,149,702 | B2 * | 12/2018 | Ewer | A61B 17/7038 |
| 10,478,239 | B2 * | 11/2019 | Agarwal | A61B 17/8605 |
| 2007/0173819 | A1 * | 7/2007 | Sandlin | A61B 17/7091 606/278 |
| 2010/0241170 | A1 * | 9/2010 | Cammisa | A61B 17/7032 606/264 |
| 2018/0168697 | A1 * | 6/2018 | Jackson | A61B 17/7038 |

* cited by examiner

*Primary Examiner* — Pedro Philogene
(74) *Attorney, Agent, or Firm* — Sorell, Lenna & Schmidt, LLP

(57) ABSTRACT

An implant receiver includes a member having an inner surface defining an implant cavity configured for disposal of a spinal implant and an outer surface. A cap includes a mating surface connectable with the outer surface such that the cap is fixed with the member and the implant is movable relative to the inner surface. In some embodiments, implants, systems, instruments and methods are disclosed.

18 Claims, 12 Drawing Sheets

SPINAL IMPLANT SYSTEM AND METHODS OF USE

TECHNICAL FIELD

The present disclosure generally relates to medical devices for the treatment of spinal disorders, and more particularly to a spinal implant system including an implant receiver and a related method.

BACKGROUND

Spinal pathologies and disorders such as kyphosis, scoliosis and other curvature abnormalities, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. Correction treatments used for positioning and alignment may employ implants such as rods, tethers and bone screws for stabilization of a treated section of a spine. Rods redirect stresses away from a damaged or defective region while healing takes place to restore proper alignment and generally support the vertebral members. This disclosure describes an improvement over these prior technologies.

SUMMARY

In one embodiment, an implant receiver is provided. The implant receiver comprises a member including an inner surface defining an implant cavity configured for disposal of a spinal implant and an outer surface. A cap includes a mating surface connectable with the outer surface such that the cap is fixed with the member and the implant is movable relative to the inner surface. In some embodiments, implants, spinal constructs, systems, instruments and methods are disclosed.

In one embodiment, a bone fastener is provided. The bone fastener comprises an implant receiver including an inner surface defining a cavity configured for disposal of a spinal rod and an outer surface. A cap includes a mating surface connectable with the outer surface such that the cap is fixed with the implant receiver and the spinal rod is movable relative to the inner surface. A shaft is configured to engage tissue. The shaft includes a head being manually engageable with the implant receiver in a non-instrumented assembly.

In one embodiment, the implant receiver comprises a closed member including an inner surface defining an implant cavity configured for disposal of a spinal rod. The inner surface includes a polymer such that the spinal rod is slidably engageable with the inner surface.

BRIEF DESCRIPTION OF THE DRAWINGS

The present disclosure will become more readily apparent from the specific description accompanied by the following drawings, in which.

DETAILED DESCRIPTION

Figure 1:
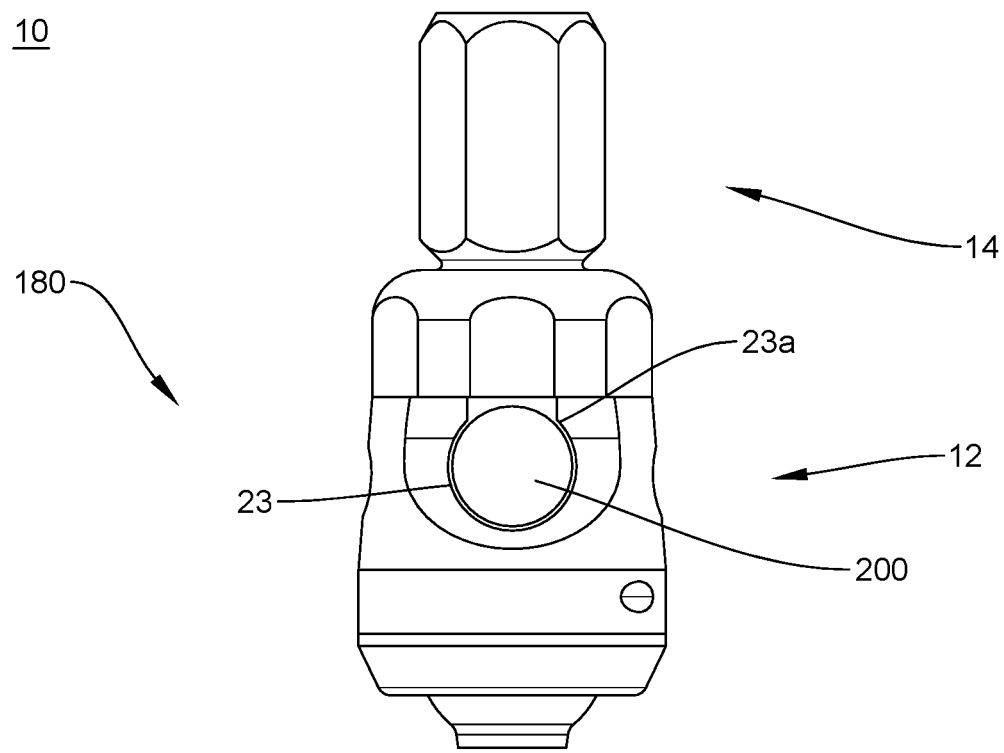
FIG. 1 is a side view of components of one embodiment of a spinal implant system in accordance with the principles of the present disclosure.

The exemplary embodiments of a surgical system and related methods of use disclosed are discussed in terms of medical devices for the treatment of musculoskeletal disorders and more particularly, in terms of a spinal implant system and method for treatment of a spine disorder. In one embodiment, the present spinal implant system includes an implant receiver comprising a member and a cap.

In some embodiments, the present system and method can be employed to treat scoliosis in a growing child and utilize a growth guidance technique, for example, a procedure that provides spinal stabilization and maintains curve correction while allowing for longitudinal spinal growth and may include, for example, growing rods, vertical expandable prosthetic titanium ribs, vertebral body stapling and/or tethers, and/or tulip head screws. In some embodiments, the present system and method be employed based on type and magnitude of spinal deformity effectively treated, age of a patient, and underlying co-morbidities, which may impact outcome. In some embodiments, the present system and method be employed with an open or closed implant receiver that include benefits such as uniform implant profile and/or ease of spinal rod placement.

In some embodiments, the present spinal implant system comprises an implant receiver, for example, connectable with a head of a screw shaft. In some embodiments, the implant receiver has an inner surface defining an implant cavity configured for disposal of a spinal implant, for example, a spinal rod. In some embodiments, the spinal implant engages the inner surface and includes a coefficient of friction in a range from about 0.04 to about 0.8. In some embodiments, the implant receiver is configured to slide along a spinal rod and includes polymer material wherein the rod is fully surrounded by polymer. In some embodiments, the polymeric head captures a spinal rod and allows it to relatively slide with reduced wear debris or other interference. In some embodiments, the present spinal implant system includes a polymeric implant receiver engageable with a non-instrumented pop-on screw assembly. In some embodiments, the polymer material includes polytetrafluoroethylene (PTFE) and/or ultra-high-molecular-weight polyethylene (UHMWPE).

In some embodiments, the implant receiver comprises a cap including a mating surface connectable with an outer surface of a member, such as, for example, a head such that the cap is fixed with the head and a spinal implant is movable relative to the inner surface. In some embodiments, the implant receiver includes a cap that maintains arms of an implant receiver from splaying. The mating surface includes a threaded surface engageable with the outer surface, forming a threaded cap polymer head.

In some embodiments, the implant receiver comprises a cap wherein the mating surface is engageable with the outer surface in a snap-fit assembly, forming a snap-on cap polymer head. In some embodiments, the mating surface includes an inner circumferential projection that defines a groove configured for disposal of the outer surface. In some embodiments, the cap is snap-fit and expandable. In some embodiments, the cap includes at least one slot for expansion. In some embodiments, the implant receiver comprises a cap that includes a plurality of equidistantly spaced radial slots. In some embodiments, the cap includes a plurality of equidistantly spaced, axially oriented circumferential slots. In some embodiments, the implant receiver is monolithically formed with a threaded shaft allowing for a smaller screw assembly. In some embodiments, the implant receiver is manually engageable with a head of the threaded shaft in a non-instrumented assembly.

In some embodiments, the present spinal implant system comprises an implant receiver with an inner surface including spaced apart arms that define an arcuate, transverse channel of an implant cavity. In some embodiments, the channel is configured for disposal of a spinal implant. In some embodiments, the implant receiver comprises a polymeric bushing disposable with the implant cavity between the inner surface and the spinal implant. In some embodiments, a polymeric bushing is placed into a metallic head of the implant receiver.

In some embodiments, the present spinal implant system comprises a bone fastener including an implant receiver having an inner surface defining a cavity configured for disposal of a spinal rod and an outer surface. In some embodiments, a cap including a mating surface is connectable with the outer surface such that the cap is fixed with the implant receiver and the spinal rod is movable relative to the inner surface. In some embodiments, the bone fastener has a screw shaft including a head being manually engageable with the implant receiver in a non-instrumented assembly. In some embodiments, the shaft is not locked and allowed to rotate freely. In some embodiments, the non-instrumented assembly includes an unlocked pop-on position, a locked pop-on position and can use an existing bone screw. In some embodiments, the implant receiver includes a polymer such that the spinal rod is slidably engageable with the inner surface. In some embodiments, the mating surface includes a threaded surface engageable with the outer surface in a snap-fit assembly.

In some embodiments, the present spinal implant system comprises an implant receiver including a closed member having an inner surface defining an implant cavity configured for disposal of a spinal rod. In some embodiments, the inner surface includes a polymer such that the spinal rod is slidably engageable with the inner surface including a coefficient of friction in a range from about 0.04 to about 0.8. In some embodiments, the closed member allows for a smaller dorsal profile.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 2:
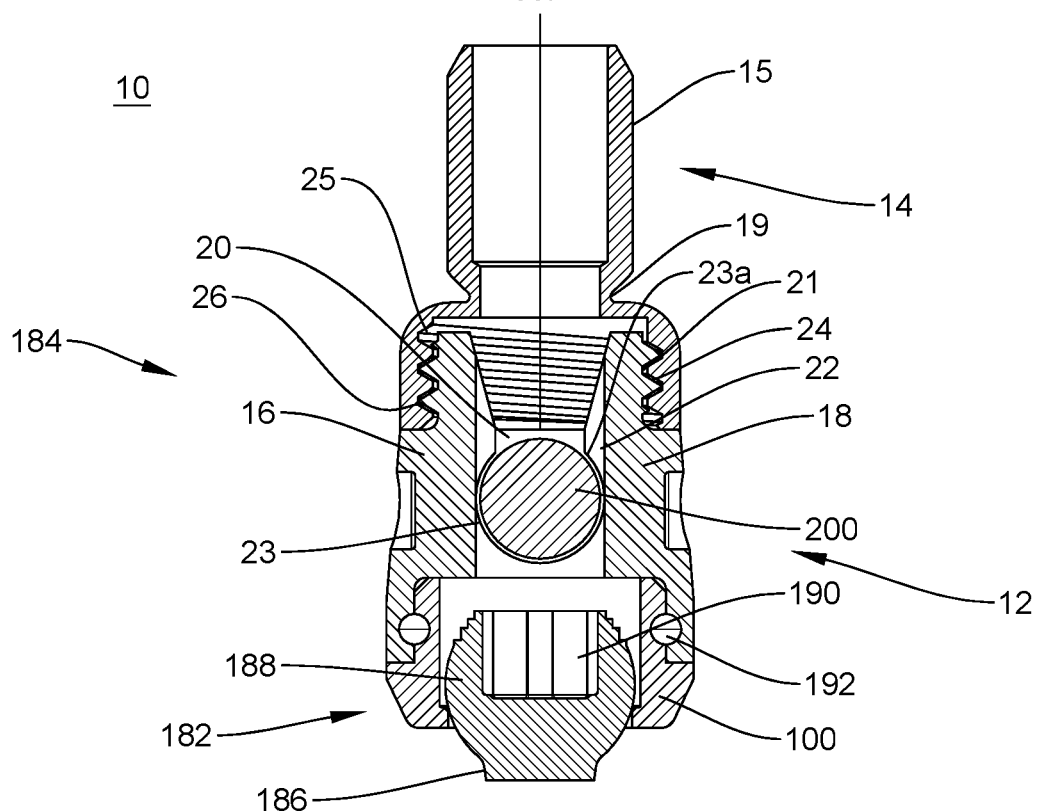
FIG. 2 is a cross section view of the components shown in FIG. 1.
Figure 3:
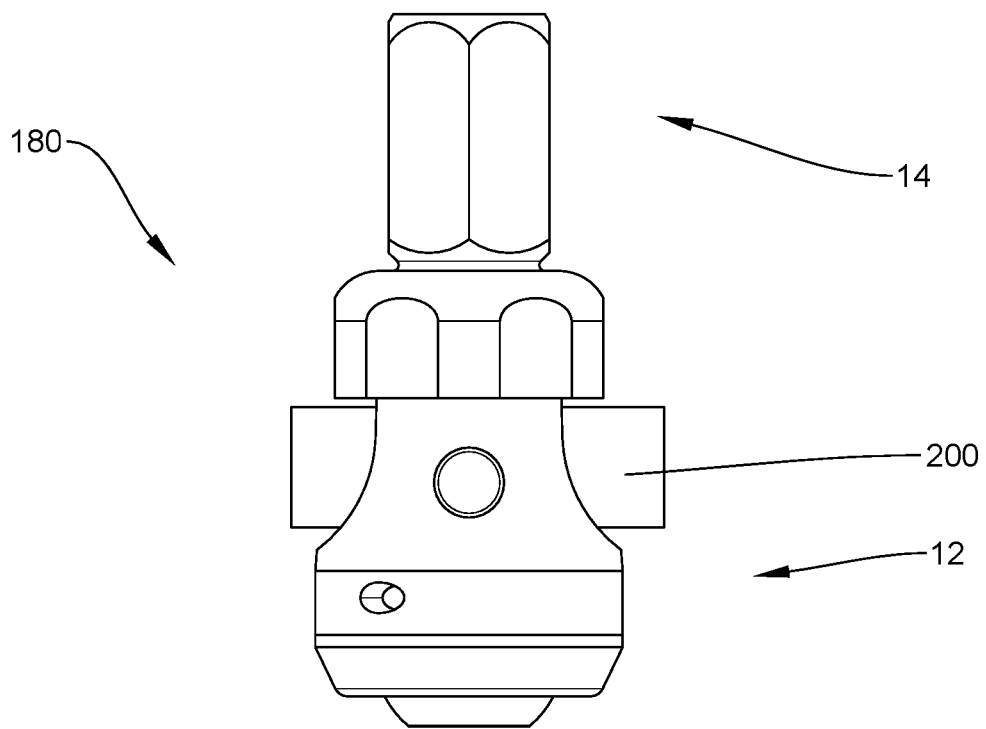
FIG. 3 is a side view of the components shown in FIG. 1.

The following discussion includes a description of a surgical system including one or more spinal implants, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-3, there are illustrated components of a surgical system, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 includes a spinal implant, for example, an implant receiver 180. Implant receiver 180 comprises a member, for example, a head 12 and a cap 14, as shown in FIG. 1. Cap 14 is connectable with head 12 such that cap 14 is fixed with head 12 and a spinal implant, for example, a spinal rod 200 is disposed with head 12. Spinal rod 200 is movable relative to head 12, as described herein, in connection with a growth guidance technique for treating a spine disorder. In some embodiments, the growth guidance technique includes a surgical procedure that provides spinal stabilization and maintains curve correction while allowing for longitudinal spinal growth along a selected path and/or orientation of vertebrae, while maintaining a force and/or load on vertebrae. In some embodiments, implant receiver 180 is configured such that spinal rod 200 is slidable relative to implant receiver 180. In some embodiments, head 12 includes a polymer material that surrounds all or a portion of an outer surface of spinal rod 200. As such, head 12 captures spinal rod 200 with a slidable polymeric surface and allows spinal rod 200 to slide relative to head 12 with reduced wear debris and/or interference. In some embodiments, the polymer material includes PTFE and/or UHMWPE.

Head 12 extends along and defines an axis X1, as shown in FIG. 2. Head 12 includes a pair of spaced apart arms 16, 18. Arms 16, 18 include an inner surface 22 of head 12 that defines an implant cavity 20 configured for disposal of spinal rod 200. In some embodiments, spinal rod 200 comprises a component of a spinal construct, as described herein. Arms 16, 18 each extend parallel to axis X1. In some embodiments, arm 16 and/or arm 18 may be disposed at alternate orientations, relative to axis X1, for example, transverse, perpendicular and/or other angular orientations such as acute or obtuse, coaxial and/or may be offset or staggered. Arms 16, 18 each include an arcuate outer surface 24 extending between a pair of side surfaces. At least one of the outer surfaces of arms 16, 18 have at least one recess or cavity configured to receive an insertion tool, compression instrument and/or instruments for inserting and tensioning implant receiver 180 with one or more components of a spinal construct, and/or vertebral tissue, as described herein. In some embodiments, one or more components of a spinal construct, as described herein, may be pre-assembled with implant receiver 180.

Implant cavity 20 is substantially U-shaped. In some embodiments, all or only a portion of implant cavity 20 may have alternate cross section configurations, such as, for example, closed, V-shaped, W-shaped, oval, oblong, triangular, square, polygonal, irregular, uniform, non-uniform, offset, staggered, and/or tapered. Inner surface 22 includes an arcuate portion 23 having a partial circle cross-section configuration. Portion 23 is disposable about a portion of an outer surface of spinal rod 200 and includes a portion of surface 22 that is slidably engageable with the outer surface of spinal rod 200 for movement of spinal rod 200 relative to implant receiver 180, as described herein. Portion 23 defines an opening 23a for receiving and/or removal of spinal rod 200 from implant receiver 180. In some embodiments, portion 23 and/or opening 23a may be adjustable and/or flexible via relative movement or flexing of arms 16, 18 for receiving and/or removal of spinal rod 200. In some embodiments, the adjustability of flexibility of portion 23 and/or opening 23a allows a snap-fit engagement of head 12 with spinal rod 200. In some embodiments, the partial circle cross-section configuration of portion 23 may include all or a portion of a full circle, for example, a quarter or semi-circle.

Inner surface 22 includes an even or smooth surface configuration, and is slidably engageable with spinal rod 200. In some embodiments, spinal rod 200 engages inner surface 22 and includes a coefficient of friction in a range from about 0.04 to about 0.8. In some embodiments, all or only a portion of surface 22 may include or be fabricated from a polymer material, such as one or more of the polymer material examples described herein, and/or have frictional properties or relative slidable surface characteristics such as the friction and/or slidable surface properties corresponding to the material examples described herein. In some embodiments, head 12 may include separate polymer components, for example, a polymeric bushing connected with inner surface 22. In some embodiments, all or only a portion of surface 22 may have alternate surface configurations to enhance engagement with spinal rod 200, such as, for example, rough, arcuate, undulating, mesh, porous, semi-porous, dimpled and/or textured. In some embodiments, head 12 may include alternate configurations, such as, for example, closed, open and/or side access. In some embodiments, all or a portion of inner surface 22 includes an inner thread form.

Outer surface 24 includes a mating surface, for example, an external thread form 21 located adjacent a proximal portion of arms 16, 18. Thread form 21 is configured for engagement with cap 14 to retain spinal rod 200 with head 12. In some embodiments, thread form 21 may include a single thread turn or a plurality of discrete threads. In some embodiments, surface 24 may include alternate mating configurations, such as, for example, friction fit, pressure fit, locking protrusion/recess, locking keyway, clips and/or adhesive.

Cap 14 has a cylindrical configuration and includes an inner surface 25 that defines an interior cavity for receiving arms 16, 18. Inner surface 25 includes a mating surface, for example, an internal thread form 26. Thread form 26 is configured for engagement with thread form 21 to connect cap 14 with head 12 and retain spinal rod 200 with head 12. In some embodiments, thread form 26 may include a single thread turn or a plurality of discrete threads. In some embodiments, surface 25 may include alternate mating configurations, such as, for example, friction fit, pressure fit, locking protrusion/recess, locking keyway, clips and/or adhesive.

In operation, a spinal construct includes spinal rod 200 being connected with implant receiver 180. Spinal rod 200 is passed through opening 23a and disposable with implant cavity 20 such that portion 23 is disposed about the outer surface of spinal rod 200 and slidably engageable with inner surface 22. Cap 14 is connected with head 12 such that thread form 26 is connected with thread form 21 in a threaded engagement. Cap 14 is fixed with head 12 and spinal rod 200 is movable relative to inner surface 22. Implant receiver 180 is configured such that spinal rod 200 is slidably translatable within implant cavity 20 relative to implant receiver 180.

Portion 23 includes surface 22, which includes a polymer material that engages spinal rod 200 such that head 12 captures spinal rod 200 with a polymeric surface having frictional properties or relative slidable surface characteristics to allow spinal rod 200 to slide relative to head 12. In some embodiments, head 12 captures spinal rod 200 for relative movement in a configuration for dynamic axial translation relative to implant receiver 180 in response to an active and/or changing spine including growth, as described herein. In some embodiments, head 12 captures spinal rod 200 such that one or more components of the spinal construct, for example, spinal rod 200, implant receiver 180 and one or more bone fasteners adapt and/or are continuously adjustable with relative movement, as described herein, to provide dynamically responsive movement in response to motion of the spine and adjacent anatomical portions due to factors, such as growth, trauma, aging, natural load bearing and dynamic characteristics of the spine, which may include flexion, extension, rotation and lateral bending, and/or external loads, which may include axial, shear, linear, non-linear, angular, torsional, compressive and/or tensile loads applied to the body of a patient.

In some embodiments, cap 14 includes a break away portion 19 that fractures at a predetermined torque. Break away portion 19 is frangibly connected to a tool engagement surface 15 of cap 14. Break away portion 19 has reduced thickness and/or reduced diameter compared to surface 15. In some embodiments, break away portion 19 is fabricated from a fracturing and/or frangible material such that manipulation of surface 15 relative to cap 14 can fracture and separate surface 15 from cap 14 at a predetermined force and/or torque limit, as described herein. In some embodiments, as force and/or torque is applied to break away portion 19 and resistance increases, for example, due to fixation of cap 14, as described herein, with head 12, the predetermined torque and force limit is approached.

In some embodiments, implant receiver 180 is connected with a screw shaft assembly 182 via a base 100 to comprise a bone fastener 184. Screw shaft assembly 182 includes shaft 186 and head 188. Shaft 186 is configured to penetrate tissue, such as, for example, bone. Shaft 186 includes an outer surface having an external thread form. In some embodiments, the external thread form may include a single thread turn or a plurality of discrete threads. Head 188 includes a tool engaging portion 190 configured to engage a surgical tool or instrument, as described herein. Head 188 is configured for attachment with base 100 via a pressure and/or force fit connection. Base 100 includes a ring (not shown) that is fixed within a groove 192 of head 12 to resist and/or prevent disengagement of the ring from groove 192 to permanently assemble screw shaft assembly 182 with head 12. In some embodiments, implant receiver 180 is connected with screw shaft assembly 182 such that bone fastener 184 includes a selected movement configuration, for example, multi-axial movement, sagittal angulation movement, fixed axis movement, mono-axial movement and/or uni-planar movement.

In some embodiments, spinal implant system 10 can include one or a plurality of bone fasteners 184, bone fasteners 194 described herein and/or fixation elements, which may be employed with a single vertebral level or a plurality of vertebral levels. In some embodiments, bone fasteners 184, 194 may be engaged with vertebrae in various orientations, such as, for example, series, parallel, offset, staggered and/or alternate vertebral levels. In some embodiments, bone fasteners 184, 194 may be configured as multi-axial screws, sagittal angulation screws, pedicle screws, mono-axial screws, uni-planar screws, fixed screws, anchors, tissue penetrating screws, conventional screws, expanding screws. In some embodiments, bone fasteners 184, 194 may be employed with wedges, anchors, buttons, clips, snaps, friction fittings, compressive fittings, expanding rivets, staples, nails, adhesives, posts, connectors, fixation plates and/or post.

Figure 4:
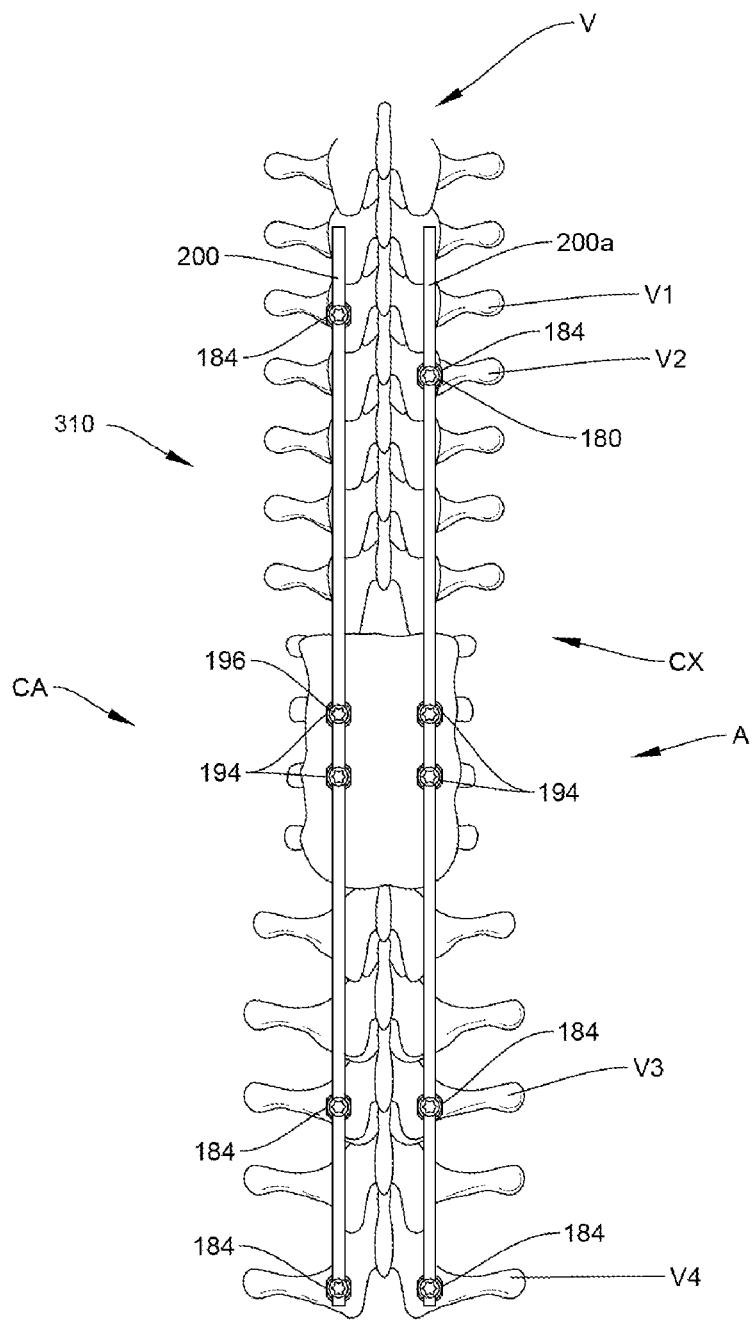
FIG. 4 is a plan view of components of one embodiment of a surgical system in accordance with the principles of the present disclosure disposed with vertebrae.
Figure 5:
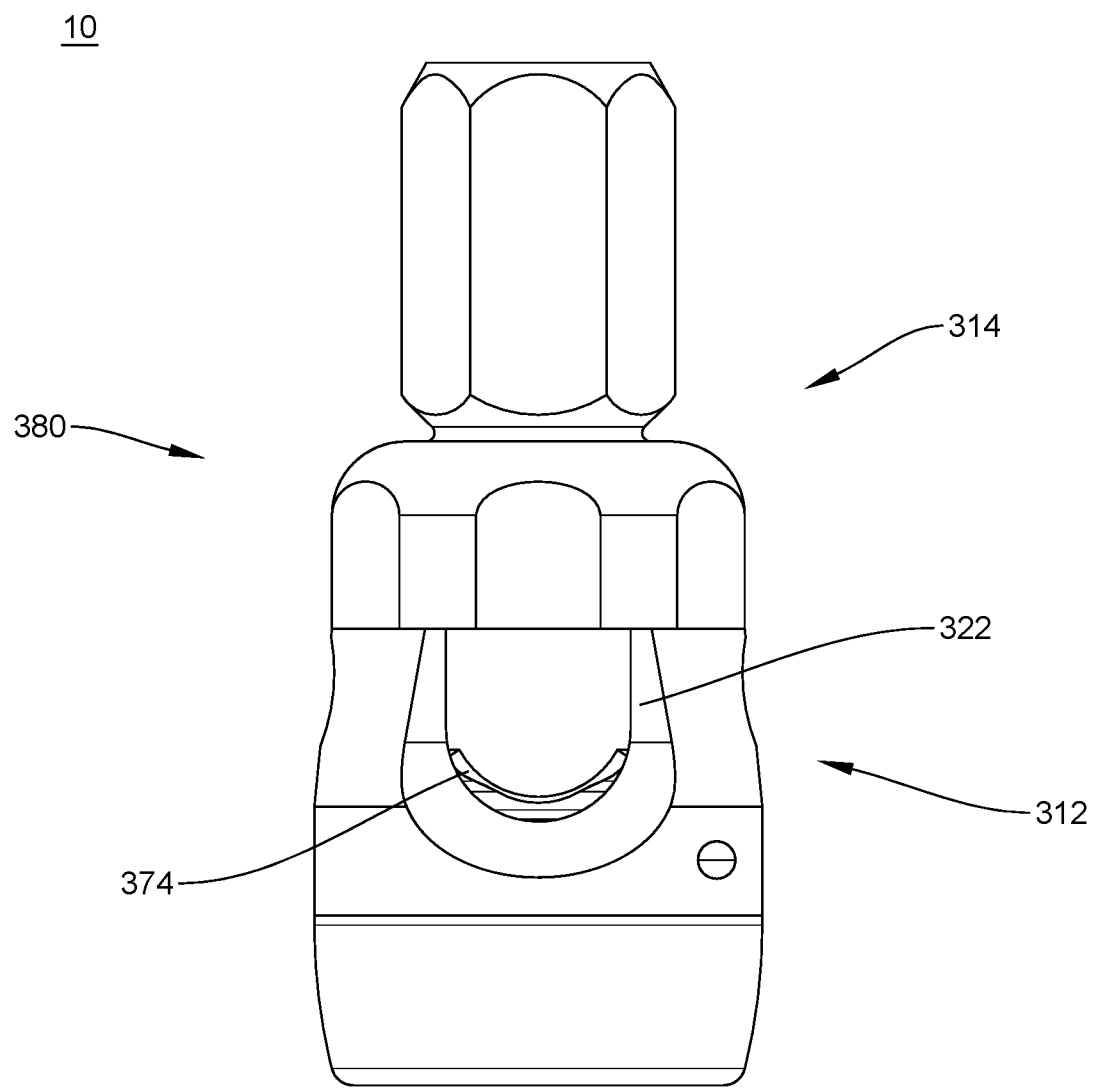
FIG. 5 is a side view of components of one embodiment of a spinal implant system in accordance with the principles of the present disclosure.
Figure 6:
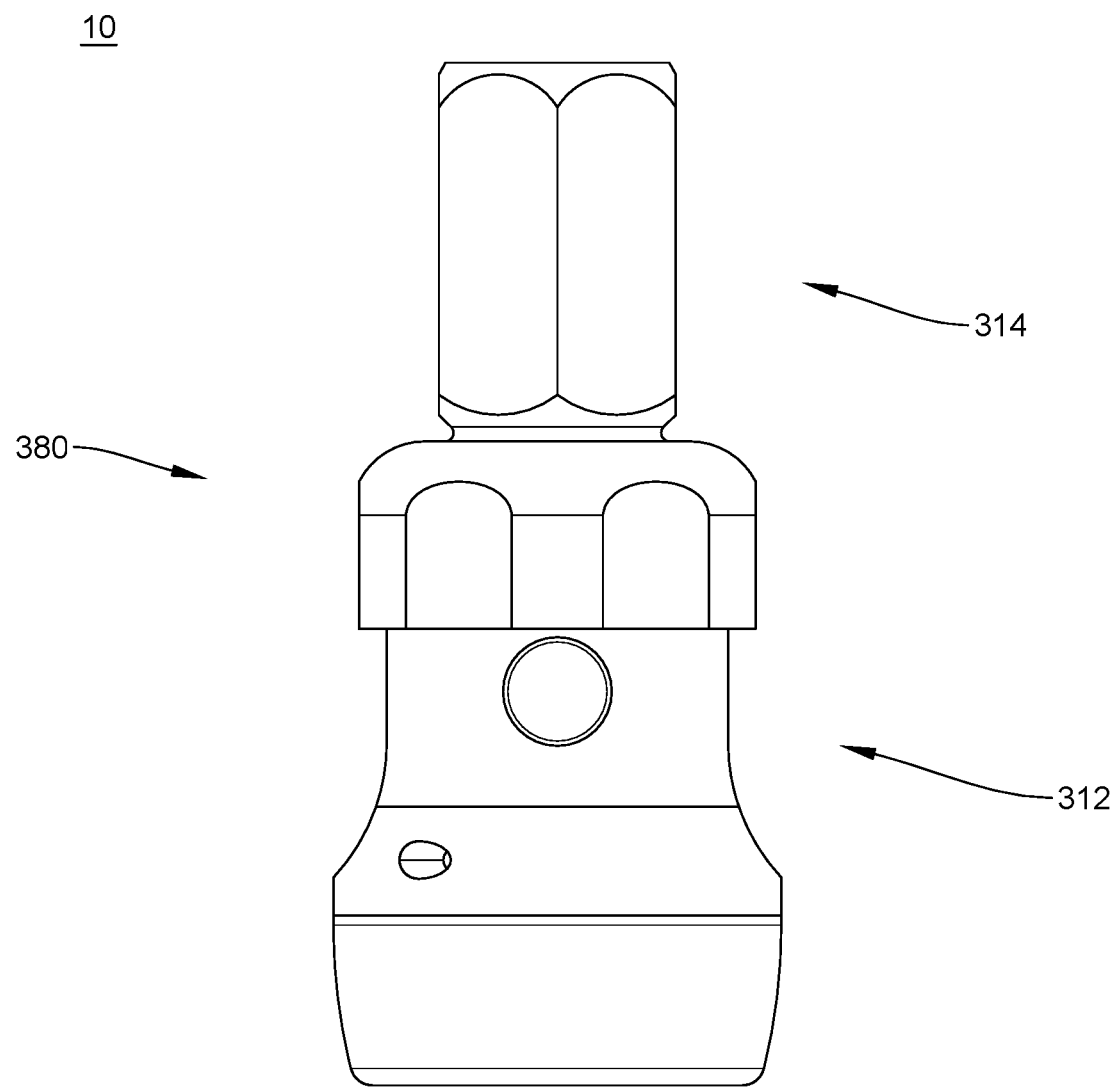
FIG. 6 is a side view of the components shown in FIG. 5.

In assembly, operation and use, as shown in FIG. 4, spinal implant system 10, similar to the systems and methods described herein, includes a spinal construct 310 and is employed with and/or subsequent to a surgical correction procedure, similar to those described herein. Spinal implant system 10 may be employed in surgical procedures for treating disorders of the spine, for example, a correction treatment to treat child/adolescent idiopathic scoliosis and/or Scheuermann's kyphosis of a spine. In some embodiments, one or all of the components of spinal implant system 10 can be delivered as a pre-assembled device or can be assembled in situ.

The surgical correction treatment including spinal construct 310 is used for correction and alignment in stabilization of a treated section of vertebrae V. In use, to create tension along vertebrae V with rods 200, 200a, a medical practitioner obtains access to a surgical site including vertebrae V via a posterior surgical approach. In some embodiments, the surgical site may be accessed in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. In some embodiments, spinal construct 310 includes one or more components, as described herein, disposed in a selected orientation, as described herein, to guide growth along a selected path and/or orientation along vertebrae V, while maintaining a force and/or load on vertebrae V. In some embodiments, one or more rods 200, 200a are disposed in a linear orientation along vertebrae V. In some embodiments, one or more rods 200, 200a are disposed with vertebrae V in alternate orientations relative to each other, such as, for example, parallel, perpendicular, adjacent, co-axial, arcuate, offset, staggered, transverse, angular and/or relative posterior/anterior orientations and/or at alternate vertebral levels.

In some embodiments, spinal implant system 10 comprises components of spinal construct 310 disposed in a bilateral configuration in connection with a growth guidance technique for treating a spine disorder. For example, a bilateral configuration can include a first spinal rod affixed to a convex side of each of a plurality of vertebrae V and a second spinal rod affixed to a concave side of each of a plurality of vertebrae V. This configuration prevents growth of vertebrae V of the convex side of the spine while allowing for growth and adjustments to the concave side for the correction treatment. In some embodiments, this growth guidance technique provides spinal stabilization and maintains curve correction while allowing for longitudinal spinal growth along a selected path and/or orientation of vertebrae V, while maintaining a force and/or load on vertebrae V.

Pilot holes are made in selected vertebrae V1, V2, V3, V4 and adjacent an apex A of a spinal curvature of vertebrae V in the selected orientation. Fixed axis bone fasteners 194 are aligned with the pilot holes and engaged with vertebrae including fixation adjacent apex A. In some embodiments, bone fasteners 194 are placed at vertebral levels in pedicles adjacent apex A for correction and maintenance of correction. Bone fasteners 184, as described herein, are aligned with the pilot holes and fastened with the tissue of vertebrae V1, V2, V3, V4.

The components of spinal construct 310 are connected with bone fasteners 184, 194 and disposed in the selected orientation with vertebrae V1, V2, V3, V4 and adjacent apex A. Spinal rod 200a is fixed with each of bone fasteners 194 via set screws 196 and disposed with each of implant receivers 180 of bone fasteners 184 connected with the vertebrae of a convex side CX of vertebrae V. Spinal rod 200 is fixed with each of bone fasteners 194 via set screws 196 and disposed with each of implant receivers 180 of bone fasteners 184 connected with the vertebrae a concave side CA of vertebrae V. This configuration prevents growth of vertebrae of convex side CX of the spine while allowing for growth and adjustments to concave side CA for a correction treatment to treat various spine pathologies, for example, adolescent idiopathic scoliosis and Scheuermann's kyphosis.

Each of spinal rods 200, 200a are connected with implant receivers 180 disposed with sides CX, CA, respectively, as described herein. Caps 14 are fixed with heads 12 and each of spinal rods 200, 200a are slidably translatable within implant cavity 20 relative to implant receiver 180. Spinal rods 200, 200a are each captured with a polymeric surface having frictional properties or relative slidable surface characteristics, as described herein, to allow spinal rods 200, 200a to slide relative to their respective head 12. In some embodiments, each implant receiver 180 captures spinal rod 200 or spinal rod 200a for relative movement in a configuration for dynamic axial translation relative to implant receiver 180 in response to an active and/or changing spine including growth, as described herein. In some embodiments, spinal rods 200, 200a are slidable relative to implant receivers 180 and fixed with bone fasteners 194 to provide dynamically responsive movement in response to motion of the spine and adjacent anatomical portions due to factors, such as growth, trauma, aging, natural load bearing and dynamic characteristics of the spine, which may include flexion, extension, rotation and lateral bending, and/or external loads, which may include axial, shear, linear, non-linear, angular, torsional, compressive and/or tensile loads applied to the body of a patient.

In some embodiments, spinal implant system 10 includes an agent, for example, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

Upon completion of a procedure, the surgical instruments and/or tools, assemblies and non-implanted components of spinal implant system 10 are removed and the incision(s) are closed. One or more of the components of spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10. In some embodiments, spinal implant system 10 may include one or a plurality of rods, plates, connectors and/or bone fasteners for use with a single vertebral level or a plurality of vertebral levels.

In some embodiments, the components of spinal implant system 10 may be employed to treat progressive idiopathic scoliosis with or without sagittal deformity in either infantile or juvenile patients, including but not limited to prepubescent children, adolescents from 10-12 years old with continued growth potential, and/or older children whose growth spurt is late or who otherwise retain growth potential. In some embodiments, the components of spinal correction system 10 and methods of use may be used to prevent or minimize curve progression in individuals of various ages.

In one embodiment, as shown in FIGS. 5-8, spinal implant system 10, similar to the systems and methods described herein, includes an implant receiver 380, similar to implant receiver 180 described herein. Implant receiver 380 is connected with a screw shaft assembly (not shown), similar to screw shaft assembly 182, as described herein, to comprise a bone fastener (not shown).

Implant receiver 380 comprises a head 312 and a cap 314, similar to head 12 and cap 14 described herein. Cap 314 is connectable with head 312 such that cap 314 is fixed with head 312 and a spinal implant, for example, a spinal rod (not shown) is disposed with head 312, similar to that described herein. The spinal rod is movable relative to head 312, as described herein, in connection with a growth guidance technique for treating a spine disorder. In some embodiments, head 312 captures the spinal rod with an inner surface 322 having a polymer material, similar to surface 22 described herein, and allows the spinal rod to slide relative to head 312 with reduced wear debris and/or interference.

Head 312 includes a pair of spaced apart arms 316, 318, similar to arms 16, 18 described herein. Arms 316, 318 include inner surface 322 and defines an implant cavity 320 configured for disposal of the spinal rod, as described herein.

Inner surface 322 is disposable about a portion of an outer surface of the spinal rod and is slidably engageable with the outer surface of the spinal rod for movement of the spinal rod relative to implant receiver 380, as described herein. Inner surface 22 includes an even or smooth surface configuration, and is slidably engageable with the spinal rod, as described herein.

Outer surface 324, similar to outer surface 24, includes an external thread form 321 located adjacent a proximal portion of arms 316, 318. Thread form 321 is configured for engagement with cap 314 to retain the spinal rod with head 312. Cap 314 has a cylindrical configuration and includes an inner surface 325 that defines an interior cavity for receiving arms 316, 318. Inner surface 325 includes an internal thread form 326. Thread form 326 is configured for engagement with thread form 321 to connect cap 314 with head 312 and retain the spinal rod with head 312, as described herein.

Head 312 includes a retaining ring 336 configured for provisional capture of the screw shaft assembly and/or fixed connection of the components of the bone fastener, as described herein. Head 312 includes a ring 344 configured for disposal in a contracted orientation and an expanded interference orientation adjacent to a ring 336 to facilitate fixed connection of the components of the bone fastener. In some embodiments, the screw shaft assembly and head 312 are assembled in situ or prior to implant to form the bone fastener.

Head 312 includes a surface defining a groove 334. Groove 334 is configured for disposal of ring 336. Ring 336 includes a circumference that defines a gap sized to allow ring 336 to pass through a bottom of head 312 by contracting circumferentially. Head 312 includes a groove 342 configured for disposal of ring 344. Ring 344 includes a circumference that extends between ends of ring 344 to define a gap.

Head 312 includes a groove 364 configured for disposal of ring 336 and/or ring 344. Groove 364 includes a circumferential channel 366 that accommodates expansion of ring 336 and/or ring 344 and is sized to allow for expansion of ring 336 and/or ring 344 therein.

A surface 368 is disposed between groove 364 and groove 334. Surface 368 is disposed at an angle relative to axis of head 312 to define a ramp 369. Ramp 369 is inclined to facilitate translation of ring 336 between groove 334 and groove 364. In one example, ring 336 is engaged with the screw shaft assembly for translation such that ring 336 slides along ramp 369, which directs and/or guides ring 336 from groove 334 into groove 364, and expands into a provisional capture orientation with the screw shaft assembly. In another example, ring 336 is engaged with ring 344 for translation such that ring 336 slides along ramp 369, which directs and/or guides ring 336 from groove 364 into groove 334, and contracts for fixed connection of the components of the bone fastener including permanent capture of head 312 and the screw shaft assembly.

Ring 336 is resiliently biased to a contracted and/or capture orientation within groove 334 and expandable to an expanded orientation within groove 364 for provisional capture of the screw shaft assembly with head 312. Ring 336 is expandable from the contracted and/or capture orientation to the expanded orientation for assembly of the screw shaft assembly with head 312. Ring 344 is disposable in a contracted orientation within groove 342 and resiliently biased to an expanded interference orientation within groove 364. In the interference orientation, ring 344 is disposed in channel 366 and adjacent to ring 336 for abutting and/or contacting engagement therewith to resist and/or prevent translation of ring 336 from groove 334 into groove 364, and fixed connection of the components of the bone fastener including permanent capture of head 312 and the screw shaft assembly.

Figure 7:
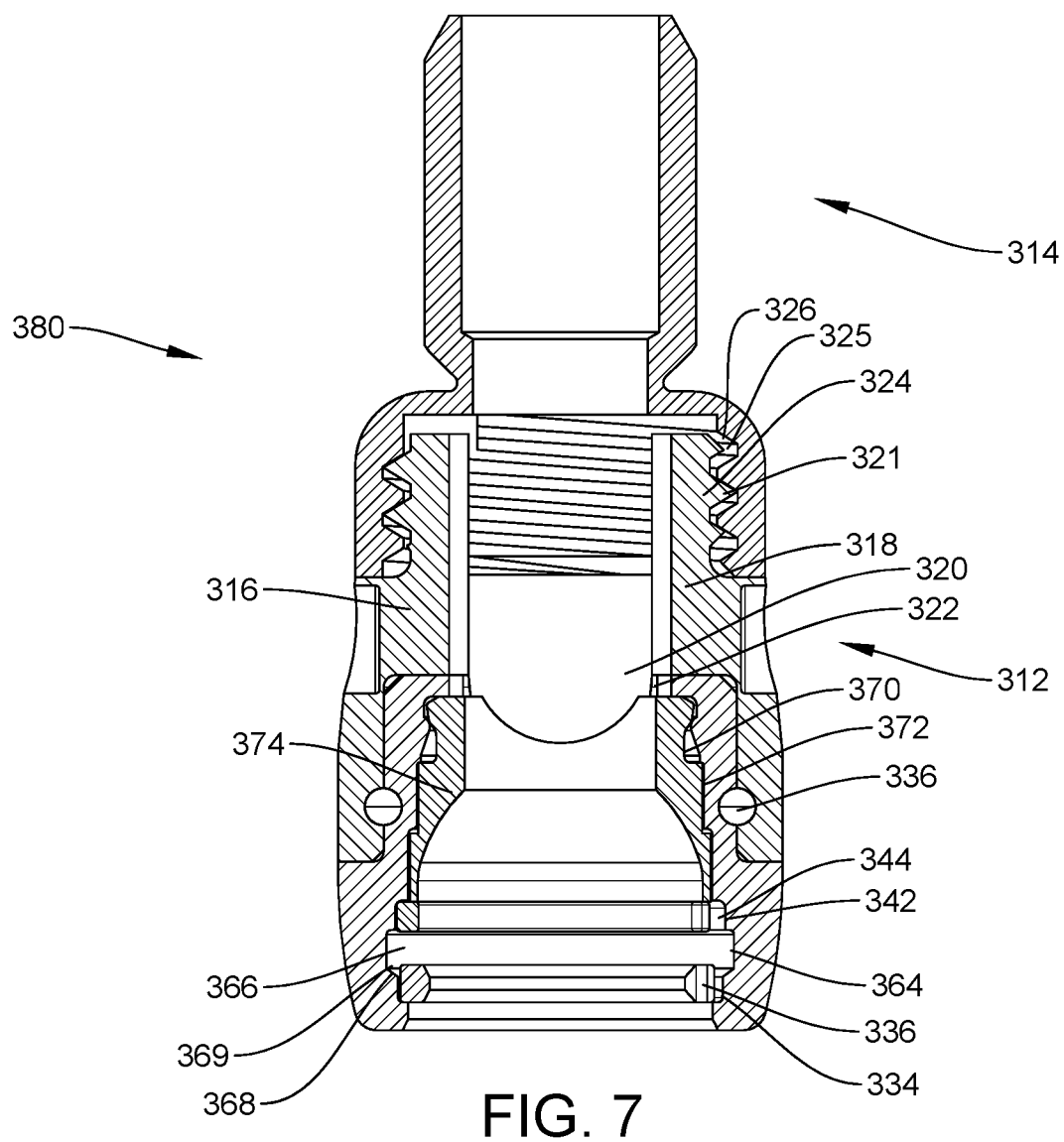
FIG. 7 is a cross section view of the components shown in FIG. 5.
Figure 8:
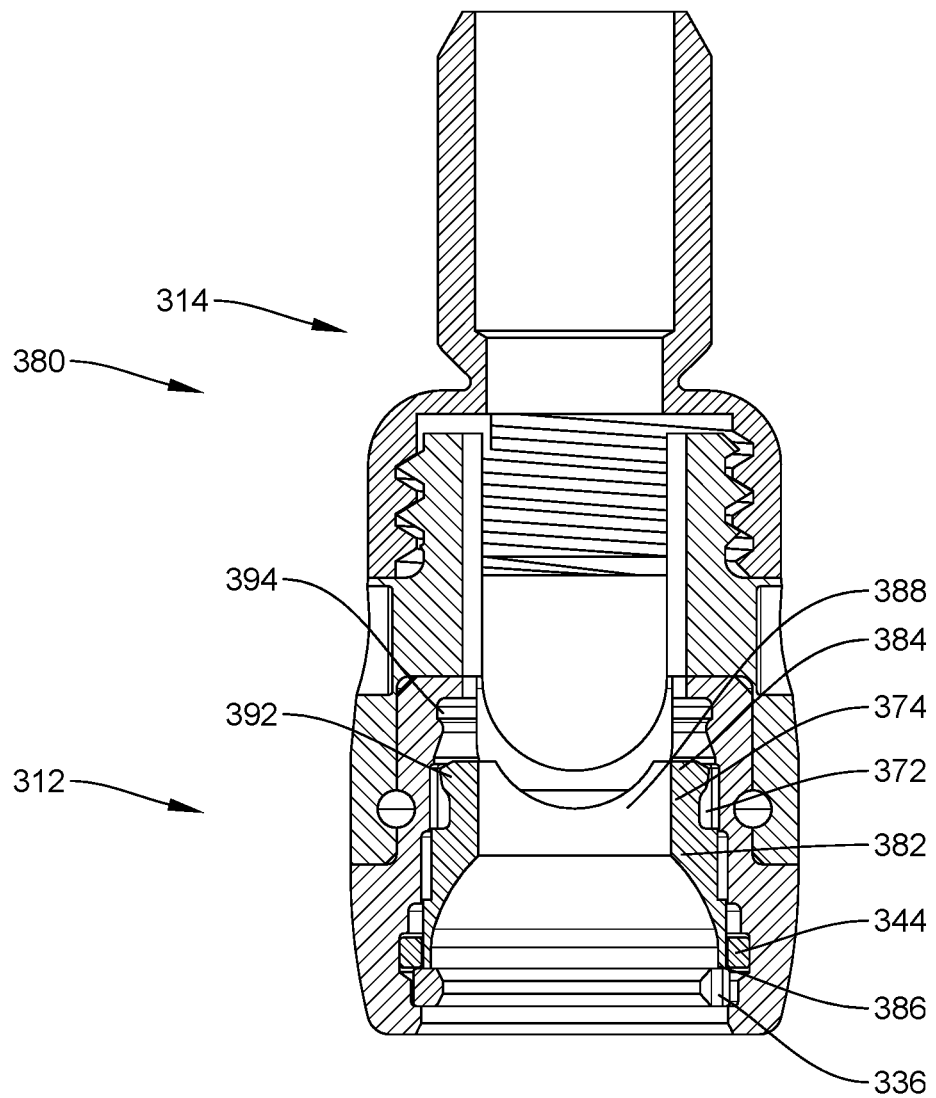
FIG. 8 is a cross section view of the components shown in FIG. 5.
Figure 9:
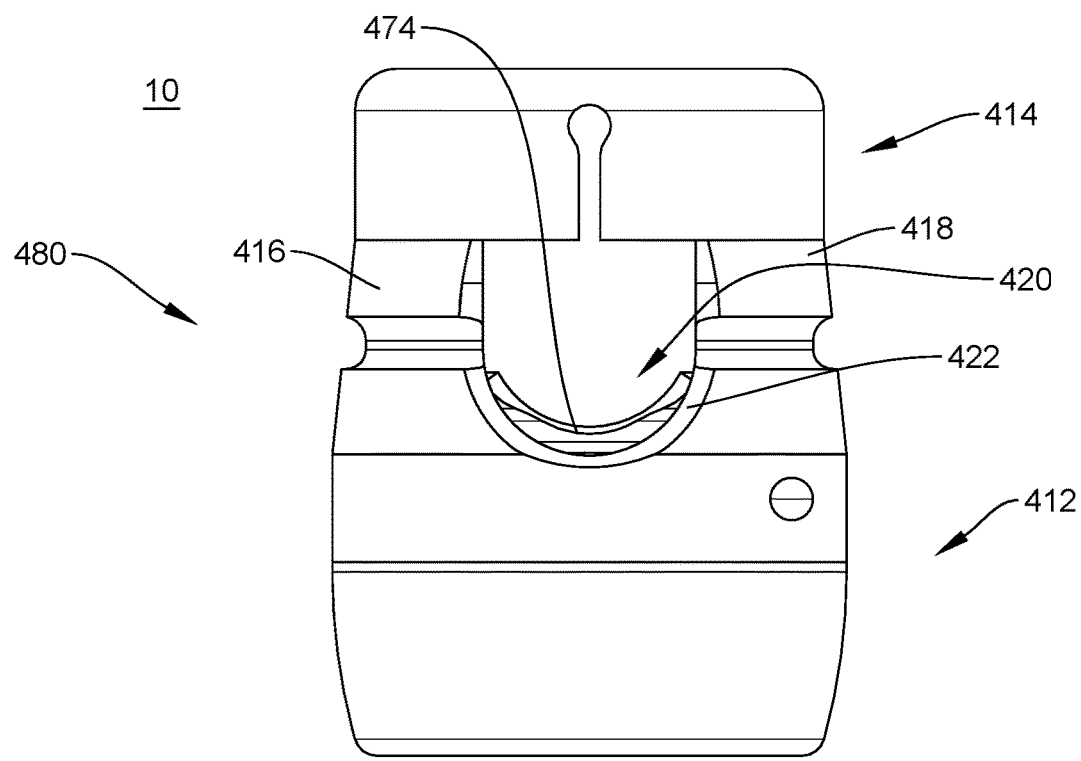
FIG. 9 is a side view of components of one embodiment of a spinal implant system in accordance with the principles of the present disclosure.

Head 312 includes a surface 370 that defines a slot 372 configured for disposal of a crown 374, as shown in FIGS. 7 and 8. Crown 374 is configured for disposal within cavity 320 and slot 372. Crown 374 includes a wall 382 having an end surface 384 and an end surface 386. Surface 384 is configured to define at least a portion 388 of cavity 320 and is slidably engageable with the outer surface of the spinal rod. In some embodiments, surface 384 includes a coefficient of friction in a range from about 0.04 to about 0.8. In some embodiments, all or only a portion of surface 384 may include or be fabricated from a polymer material, such as one or more of the polymer material examples described herein, and/or have frictional properties or relative slidable surface characteristics such as the friction and/or slidable surface properties corresponding to the material examples described herein.

Surface 384 includes a circumferential flange 392. Head 312 includes an undercut surface that defines a groove 394. Flange 392 is configured for disposal with groove 394. Engagement of flange 392 with the undercut surface that defines groove 394 retains crown 374 with head 312 in a first orientation adjacent ring 344 when ring 344 is disposed in groove 342. Translation of crown 374 into a second orientation moves ring 344 from groove 342.

Crown 374 is configured for translation within slot 372 along surface 370. Translation of crown 374 within slot 372 causes surface 386 to engage ring 344. Surface 386 is disposed adjacent ring 344 such that axial translation of crown 374 causes crown 374 to displace ring 344 from groove 342. Ring 344 is disengageable from groove 342 upon engagement with crown 374, which drives ring 344 from groove 342. As such, ring 344 is movable between the contracted orientation and the expanded interference orientation in groove 364, as described herein, to prevent migration of ring 336 from groove 334 into groove 364 for fixed connection of the components of bone fastener 484. Surface 386 is positioned with ring 344 to resist and/or prevent displacement of ring 344 from channel 366, as shown in FIG. 8.

The screw shaft assembly includes shaft and head 312, similar to screw shaft assembly 182, described herein. In some embodiments, head 312 may be disposed with the screw shaft assembly in alternate fixation configurations, such as, for example, friction fit, pressure fit, locking protrusion/recess, locking keyway and/or adhesive. In some embodiments, head 312 is configured for rotation relative to the screw shaft assembly for multi-axial movement. In some embodiments, head 312 is configured for rotation in range of 360 degrees relative to the screw shaft assembly to facilitate positioning of the shaft with tissue. In some embodiments, head 312 is configured for selective rotation in range of 360 degrees relative to and about the screw shaft assembly such that the shaft is selectively aligned for rotation in a plane relative to head 312. In some embodiments, head 312 may be disposed with the screw shaft assembly in a uni-axial configuration or a sagittally adjustable configuration.

In some embodiments, the screw shaft assembly is manually engageable with head 312 in a non-instrumented assembly, as described herein. In some embodiments, manual engagement and/or non-instrumented assembly of head 312 and the screw shaft assembly includes coupling without use of separate and/or independent instrumentation engaged with the screw shaft assembly components to effect assembly. In some embodiments, manual engagement and/or non-instrumented assembly includes a practitioner, surgeon and/or medical staff grasping head 312 and the screw shaft assembly and forcibly assembling the components. In some embodiments, manual engagement and/or non-instrumented assembly includes a practitioner, surgeon and/or medical staff grasping head 312 and the screw shaft assembly and forcibly snap fitting the components together, as described herein. In some embodiments, manual engagement and/or non-instrumented assembly includes a practitioner, surgeon and/or medical staff grasping head 312 and the screw shaft assembly and forcibly pop fitting the components together and/or pop fitting head 312 onto the screw shaft assembly, as described herein. In some embodiments, a force in a range of 2-50 N is required to manually engage head 312 and the screw shaft assembly and forcibly assemble the components. For example, a force in a range of 2-50 N is required to snap fit and/or pop fit assemble head 312 and the screw shaft assembly. In some embodiments, a force in a range of 5-10 N is required to manually engage head 312 and the screw shaft assembly and forcibly assemble the components. For example, a force in a range of 5-10 N is required to snap fit and/or pop fit assemble head 312 and the screw shaft assembly. In some embodiments, this configuration provides manually engageable components that are assembled without instrumentation, and subsequent to assembly, the assembled components have a selected pull-out strength and/or can be pulled apart, removed and/or separated with a minimum required force.

In some embodiments, spinal implant system 10 comprises a spinal implant kit, as described herein, which includes a plurality of the screw shaft assemblies and/or heads 312. The screw shaft assemblies and/or heads 312 is configured for selection such that the components of the bone fastener are interchangeable.

In one embodiment, as shown in FIGS. 9-13, spinal implant system 10, similar to the systems and methods described herein, includes an implant receiver 480, similar to implant receiver 380, as described herein. Implant receiver 480 is manually engageable with a screw shaft assembly (not shown), similar to screw shaft assembly 182, in a non-instrumented assembly, as described herein.

Implant receiver 480 comprises a head 412 and a cap 414, similar to head 12 and cap 14 described herein. Cap 414 is connectable with head 412 such that cap 414 is fixed with head 412 and a spinal implant, for example, a spinal rod (not shown) is disposed with head 412, similar to that described herein. Head 412 includes a pair of spaced apart arms 416, 418, similar to arms 16, 18 described herein. Arms 416, 418 include inner surface 422 and defines an implant cavity 420 and a surface 422, similar to cavity 20 and surface 22 described herein, configured for disposal of the spinal rod, as described herein. Cap 414 is connectable with head 412 such that cap 414 is fixed with head 412 and the spinal rod is disposed with head 412. The spinal rod is movable relative to head 412, as described herein, in connection with a growth guidance technique for treating a spine disorder. In some embodiments, head 412 captures the spinal rod with inner surface 422 and/or crown 474, which include a polymer material, similar to surface 22 and crown 374 described herein, and allows the spinal rod to slide relative to head 412 with reduced wear debris and/or interference.

Outer surface 424 includes a projection 421 located adjacent a proximal portion of arms 416, 418. Projection 421 is configured for engagement with cap 414 in a snap-fit assembly to retain the spinal rod with head 412, as described herein.

Figure 12:
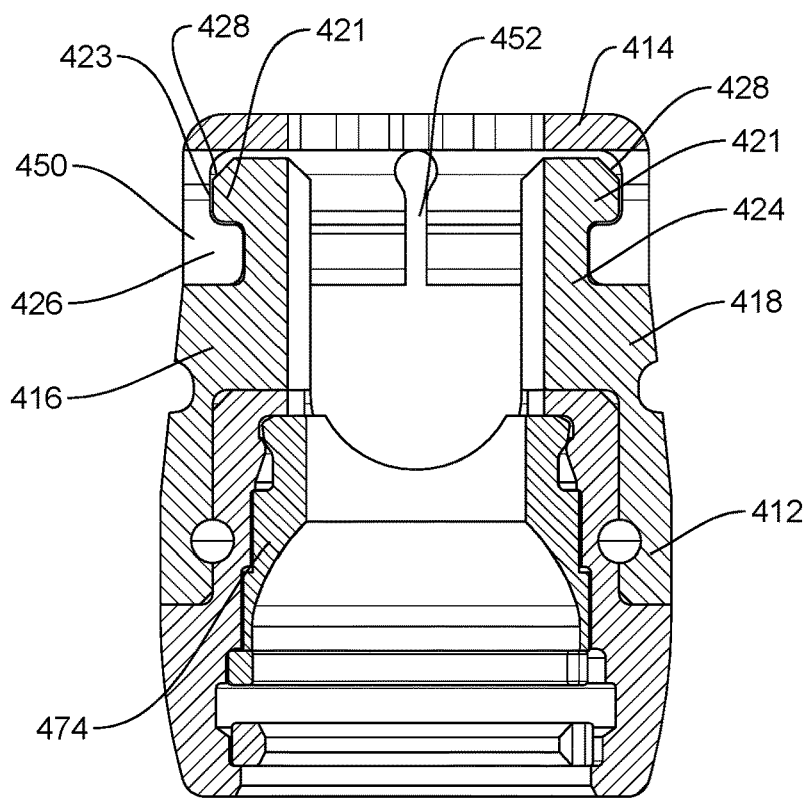
FIG. 12 is a cross section view of the components shown in FIG. 9.
Figure 13:
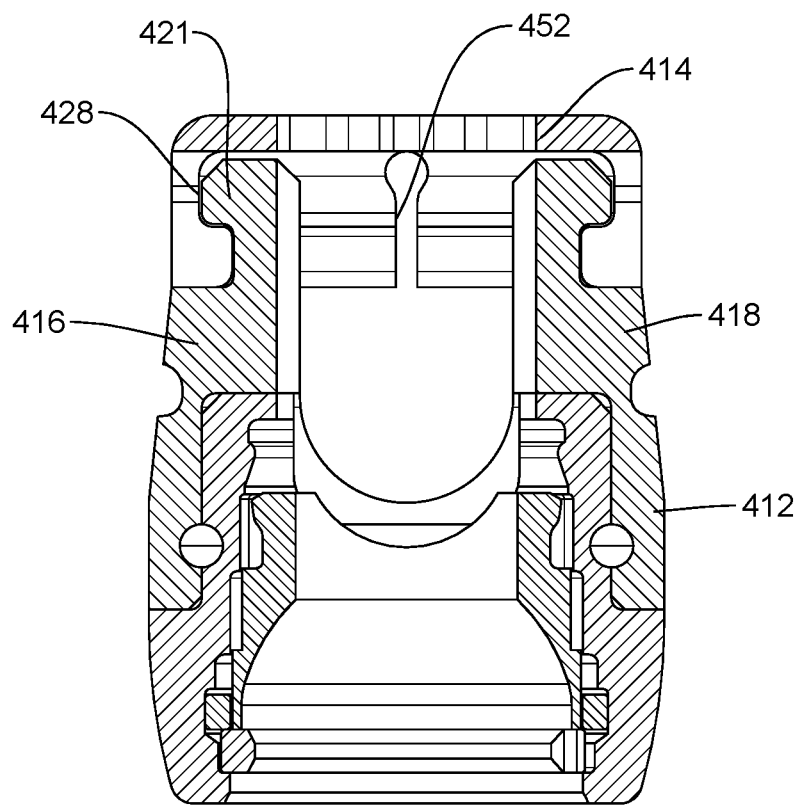
FIG. 13 is a cross section view of the components shown in FIG. 9.

Cap 414 has a cylindrical configuration and includes a wall 450 and an inner surface 423 that define an interior cavity for receiving arms 416, 418. Inner surface 423 includes an inner circumferential projection 426 extending about a distal end of wall 450, as shown in FIGS. 12 and 13. Projection 426 defines a groove 428 configured for disposal of projection 421.

Figure 10:
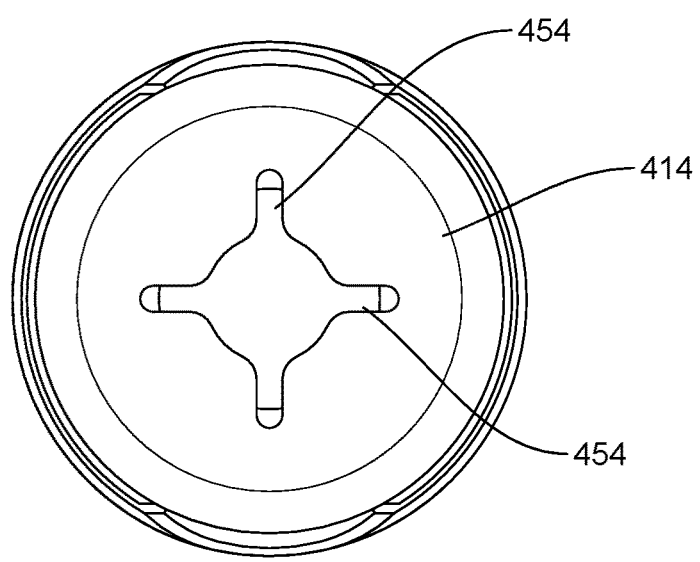
FIG. 10 is a top view of the components shown in FIG. 9.
Figure 11:
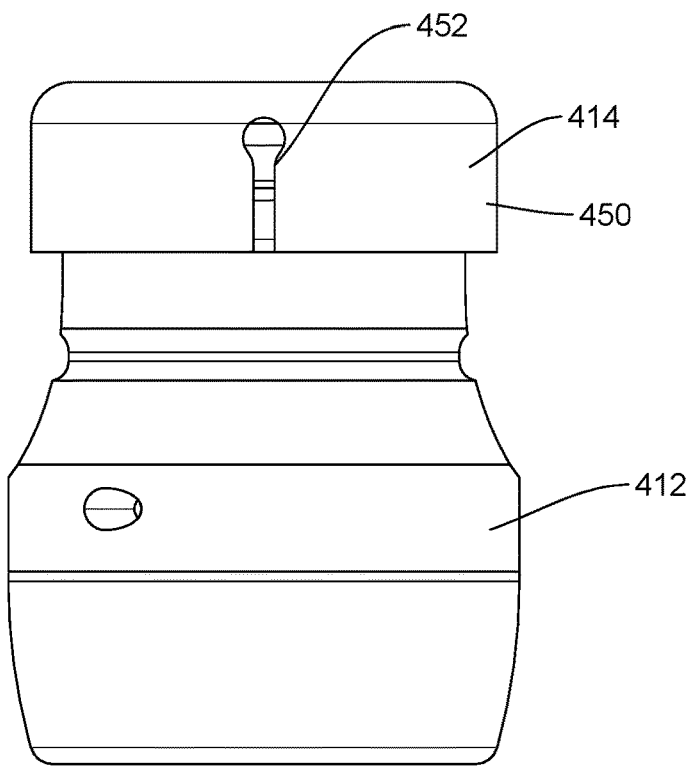
FIG. 11 is a side view of the components shown in FIG. 9.

In some embodiments, cap 414 is configured to expand to facilitate connection with head 412. For example, wall 450 includes at least one slot 452 extending longitudinally along wall 450 to facilitate expansion as wall 450 translates over arms 416, 418. In some embodiments, wall 450 includes a plurality of equidistantly spaced, axially oriented circumferential slots 452. In some embodiments, cap 414 includes a plurality of equidistantly spaced radial slots 454, as shown in FIG. 10.

Figure 14:
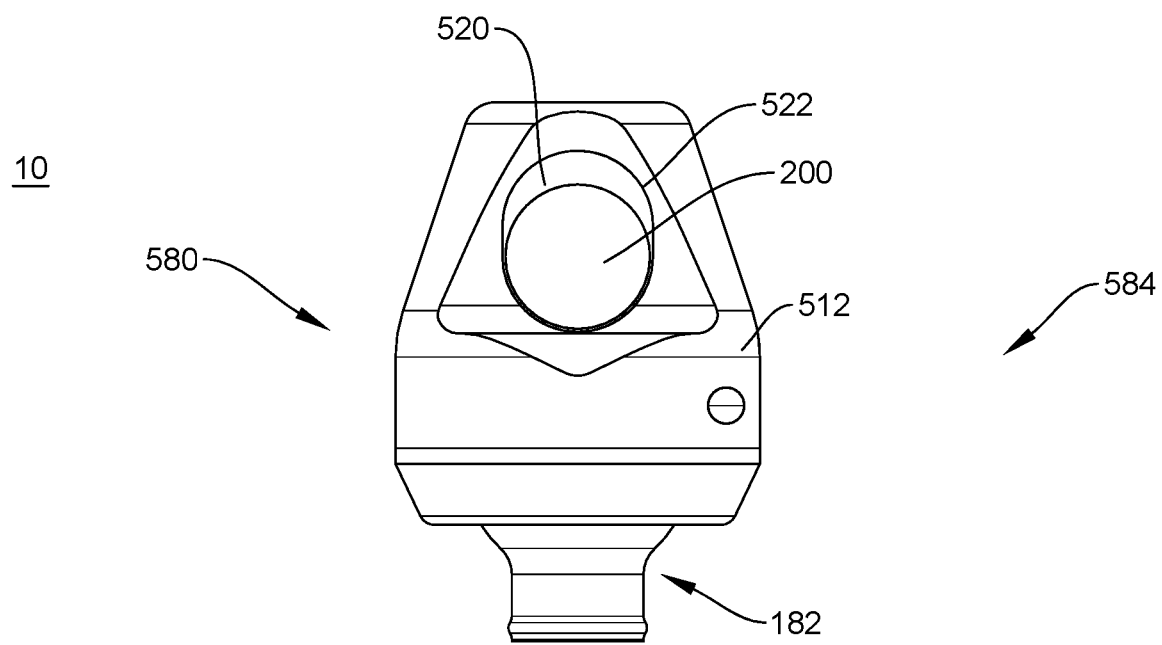
FIG. 14 is a side view of components of one embodiment of a spinal implant system in accordance with the principles of the present disclosure.
Figure 15:
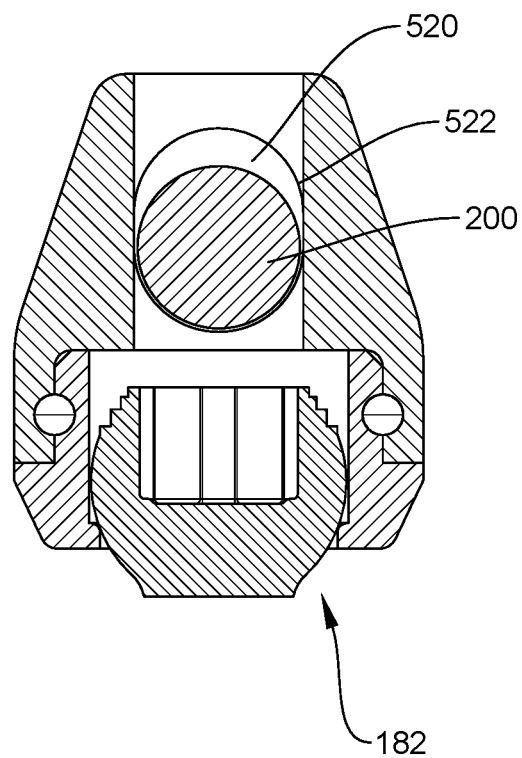
FIG. 15 is a cross section view of the components shown in FIG. 14.
Figure 16:
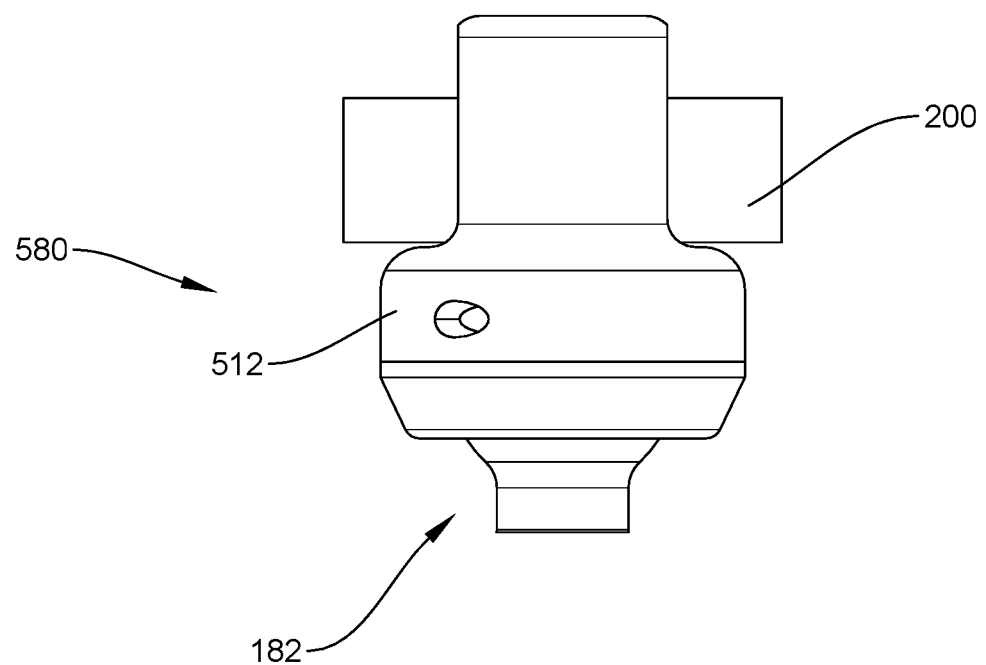
FIG. 16 is a side view of the components shown in FIG. 9.

In one embodiment, as shown in FIGS. 14-16, spinal implant system 10, similar to the systems and methods described herein, includes an implant receiver 580, similar to implant receiver 180, as described herein. Implant receiver 580 is connected with screw shaft assembly 182 via base 100, as described herein, to comprise a bone fastener 584.

Implant receiver 580 comprises a head 512, as shown in FIG. 14. Head 12 has a closed configuration to circumferentially enclose spinal rod 200 described herein. Spinal rod 200 is movable relative to head 512, as described herein, in connection with a growth guidance technique for treating a spine disorder. In some embodiments, implant receiver 580 is configured such that spinal rod 200 is slidable relative to implant receiver 580. In some embodiments, head 512 includes a polymer material that surrounds all of spinal rod 200. As such, head 512 captures spinal rod 200 with inner surface 522, which includes a polymer material similar to surface 22 described herein, and allows spinal rod 200 to slide relative to head 512 with reduced wear debris and/or interference.

Inner surface 522 defines an implant cavity 520 configured for disposal of spinal rod 200. Implant cavity 520 is substantially oblong circular. In some embodiments, all or only a portion of implant cavity 520 may have alternate cross section configurations, such as, for example, closed, V-shaped, W-shaped, oval, oblong, triangular, square, polygonal, irregular, uniform, non-uniform, offset, staggered, and/or tapered. Inner surface 522 is slidably engageable with the outer surface of spinal rod 200 for movement of spinal rod 200 relative to implant receiver 580, as described herein. Inner surface 522 includes an even or smooth surface configuration, and is slidably engageable with spinal rod 200, as described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An implant receiver comprising:
   a member comprising a proximal portion and a distal portion removably coupled to the proximal portion, the proximal portion including an inner surface and a threaded outer surface, the inner surface defining a portion of an implant cavity, the implant cavity being configured for disposal of a spinal implant, the distal portion comprising an inner surface defining an aperture;
   a crown disposed in the aperture such that a proximal surface of the crown directly engages the inner surface of the distal portion and defines a portion of the implant cavity; and
   a cap including a body, a projection and a flange, the projection and the flange each extending from the body such that the flange extends about the projection, the flange having a threaded inner surface connectable with the threaded outer surface to couple the cap with the member such that the projection is positioned in the implant cavity and the implant is movable relative to the inner surface of the proximal portion.

2. An implant receiver as recited in claim 1, wherein the member includes a polymer such that the implant is slidably engageable with the inner surface of the proximal portion.

3. An implant receiver as recited in claim 1, wherein the implant engages the inner surface of the proximal portion and includes a coefficient of friction in a range from about 0.04 to about 0.8.

4. An implant receiver as recited in claim 1, wherein the inner surface of the proximal portion includes spaced apart arms, the arms and the proximal surface of the crown defining an arcuate, transverse channel of the implant cavity, the channel being configured for disposal of the implant.

5. An implant receiver as recited in claim 1, wherein the proximal portion includes a first groove, the distal portion includes a second groove and the implant receiver comprises a retaining ring positioned in the grooves to removably couple the proximal portion to the distal portion.

6. An implant receiver as recited in claim 1, wherein the proximal portion includes a first body and a first flange extending from a distal end of the first body, the distal portion including a second body and a second flange extending from a proximal end of the second body, the proximal portion being coupled to the distal portion such that the second flange is disposed within a cavity defined by the first flange.

7. An implant receiver as recited in claim 1, wherein the proximal portion includes a first body and a first flange extending from a distal end of the first body, the distal portion including a second body and a second flange extending from a proximal end of the second body, the proximal portion being coupled to the distal portion such that an inner surface of the first flange directly engages an outer surface of the second flange.

8. An implant receiver as recited in claim 1, wherein the proximal portion includes a first body and a first flange extending from a distal end of the first body, proximal portion including a first groove extending into an inner surface of the first flange, the distal portion including a second body and a second flange extending from a proximal end of the second body, the distal portion including a second groove extending into an outer surface of the second flange, the implant receiver comprising a retaining ring disposed in the grooves to couple the proximal portion to the distal portion.

9. An implant receiver as recited in claim 1, wherein the projection is coaxial with the aperture when the threaded inner surface is mated with the threaded outer surface to couple the cap with the member.

10. An implant receiver as recited in claim 1, wherein the flange extends 360 degrees about the projection.

11. An implant receiver as recited in claim 1, wherein the projection is cylindrical and includes an outer surface, the outer surface of the projection defining a helical thread form.

12. An implant receiver as recited in claim 1, wherein the projection is tapered and includes an outer surface, the outer surface of the projection defining a helical thread form.

13. An implant receiver as recited in claim 1, wherein the body extends along a central longitudinal axis between opposite proximal and distal surfaces, the projection and the flange each extending from the distal surface such that the projection is coaxial with the central longitudinal axis.

14. An implant receiver as recited in claim 1, wherein the body extends along a central longitudinal axis between opposite proximal and distal surfaces, the projection and the flange each including a proximal end surface coupled to the distal surface and an opposite distal end surface, the distal end surface of the flange being aligned with the distal end surface of the projection along a transverse axis, the transverse axis extending perpendicular to the central longitudinal axis.

15. An implant receiver as recited in claim 1, wherein the body extends along a central longitudinal axis between opposite proximal and distal surfaces, the projection and the flange each including a proximal end surface coupled to the distal surface and an opposite distal end surface, the distal end surface of the projection being planar and extending perpendicular to the central longitudinal axis.

16. An implant receiver comprising:
   a member comprising a proximal portion and a distal portion removably coupled to the proximal portion, the proximal and distal portions each being monolithic, the proximal portion including spaced apart arms having threaded outer surfaces, inner surfaces of the arms defining a portion of an implant cavity, the implant cavity being configured for disposal of a spinal implant, the distal portion comprising an inner surface defining an aperture;

a monolithic crown disposed in the aperture such that a top surface of the crown directly engages the inner surface of the distal portion and defines a portion of the implant cavity; and a monolithic cap including a body, a central projection and a circumferential flange, the projection and the flange each extending from the body such that the flange extends about the projection and the flange is spaced apart from the projection by the body, the flange having a threaded inner surface configured for engagement with the threaded outer surfaces to couple the cap to the proximal portion such that the projection is positioned in the implant cavity, the projection having a threaded outer surface, the threaded outer surface of the projection facing the threaded inner surface of the flange.

17. An implant receiver as recited in claim 16, wherein a bottom surface of the crown defines a cavity configured for disposal of a head of a screw shaft.

18. An implant receiver comprising:
a member comprising a proximal portion and a distal portion removably coupled to the proximal portion, the proximal and distal portions each being monolithic, the proximal portion including spaced apart arms having threaded outer surfaces, inner surfaces of the arms defining a portion of an implant cavity, the implant cavity being configured for disposal of a spinal implant, the distal portion comprising an inner surface defining an aperture;

a crown disposed in the aperture such that a top surface of the crown directly engages the inner surface of the distal portion and defines a portion of the implant cavity and a bottom surface of the crown defines a cavity configured for disposal of a head of a screw shaft; and a monolithic cap including a body, a central projection and a circumferential flange, the projection and the flange each extending from a distal end of the body such that the flange extends 360 degrees about the projection and the flange is spaced apart from the projection by the body, the flange having a threaded inner surface of the cap that engages the threaded outer surfaces to couple the cap to the proximal portion such that a planar distal end of the projection is positioned in the implant cavity, the cap being monolithic.

\* \* \* \* \*